US011193152B2

(12) United States Patent
Han et al.

(10) Patent No.: US 11,193,152 B2
(45) Date of Patent: Dec. 7, 2021

(54) RECOMBINANT MICROORGANISM HAVING ENHANCED ABILITY TO PRODUCE HEME, COPROPORPHYRIN III, AND UROPORPHYRIN III, AND METHOD FOR PRODUCING HEME, COPROPORPHYRIN III, AND UROPORPHYRIN III USING SAME

(71) Applicant: Korea University Research and Business Foundation, Seoul (KR)

(72) Inventors: Sung Ok Han, Seoul (KR); Young-jin Ko, Chuncheon-si (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/611,929

(22) PCT Filed: May 18, 2018

(86) PCT No.: PCT/KR2018/005740
§ 371 (c)(1),
(2) Date: Nov. 8, 2019

(87) PCT Pub. No.: WO2018/212626
PCT Pub. Date: Nov. 22, 2018

(65) Prior Publication Data
US 2020/0270658 A1    Aug. 27, 2020

(30) Foreign Application Priority Data

May 18, 2017   (KR) .................. 10-2017-0061713
May 18, 2018   (KR) .................. 10-2018-0056906

(51) Int. Cl.
*C12N 1/21*    (2006.01)
*C12N 9/02*    (2006.01)
*C12N 9/90*    (2006.01)
*C07K 14/34*   (2006.01)
*C12P 9/00*    (2006.01)
*C12P 17/18*   (2006.01)

(52) U.S. Cl.
CPC ........... *C12P 17/182* (2013.01); *C07K 14/34* (2013.01); *C12N 9/0008* (2013.01); *C12N 9/90* (2013.01); *C12Y 102/0107* (2013.01); *C12Y 504/03008* (2013.01)

(58) Field of Classification Search
None
See application file for complete search history.

(56) References Cited

U.S. PATENT DOCUMENTS

2016/0319272 A1* 11/2016 Kang ................. C12N 15/1031

FOREIGN PATENT DOCUMENTS

| KR | 10-0459918 B1   | 12/2004 |
| KR | 10-2013-0075319 A | 7/2013 |
| KR | 10-1326255 B1   | 11/2013 |
| KR | 10-2014-0058046 A | 5/2014 |
| KR | 10-1756338 B1   | 7/2017 |

OTHER PUBLICATIONS

Choi et al., "Heme Derived from Corynebacterium glutamicum: A Potential Iron Additive for Swine and an Electron Carrier Additive for Lactic Acid Bacterial Culture", J. Microbiol. Biotechnol. 27:500-506, Mar. 2017 (Year: 2017).*
Ramzi et al. "5-Aminolevulinic acid production in engineered Corynebacterium glutamicum via C5 biosynthesis pathway", Enzyme Microb. Technol. 81:1-7, 2015 (Year: 2015).*
Yu et al., Microb. Cell. Fact. 14:183, 2015, 10 pages (Year: 2015).*
UniProt Database Accession No. Q8NP95, Mar. 2017, 2 pages (Year: 2017).*
Brune et al., BMC Genomics 7:21, 2006, 19 pages (Year: 2006).*
UniProt Database Accession No. A7ZHP6, Apr. 2017, 2 pages (Year: 2017).*
Beale, Samuel I. et al., "The Biosynthesis of δ-Aminolevulinic Acid in Higher Plants", *Plant Physiology*, vol. 53, 1974, (pp. 297-303).
Beale, Samuel I. et al., "Chemical Synthesis of 4,5-Dioxovaleric Acid and Its Nonenzymatic Transamination to 5-Aminolevulinic Acid", *Phytochemistry*, vol. 18, Issue 3, 1979 (pp. 441-444).
"Chapter I: Prevention of iron deficiency with hemoglobin-iron. A review of studies of the absorption of heme and non-heme iron", *Acta Medica Scandinavica*, vol. 205, Issue S629, Jan./Dec. 1979 (pp. 7-20).
"Chapter II: Hemoglobin fortification of food. Absorption of hemoglobin and non-heme iron", *Acta Medica Scandinavica*, vol. 205, Issue S629, Jan./Dec. 1979 (pp. 21-30).
"Chapter III: Intestinal absorption of heme iron in man", *Acta Medica Scandinavica*, vol. 205, Issue S629, Jan./Dec. 1979 (pp. 31-44).
"Chapter IV: Nutritional value of blood proteins", *Acta Medica Scandinavica*, vol. 205, Issue S629, Jan./Dec. 1979 (pp. 45-46).
"Acknowledgments", *Acta Medica Scandinavica*, vol. 205, Issue S629, Jan./Dec. 1979 (pp. 47).
"Kipe-Nolt, Judith A. et al., "Biosynthesis of δ-Aminolevulinic Acid from Glutamate in Agmenellum quadruplicatum, *Plant Physiology*, vol. 65, 1980 (pp. 126-128).
Jaenchen, Rolf et al., Inhibition of factor F430 synthesis by levulinic acid in Methanobacterium thermoautotrophicum, *FEMS Microbiology Letters*, vol. 12, Issue 2, Oct. 1981, (pp. 167-170).

(Continued)

*Primary Examiner* — David Steadman
(74) *Attorney, Agent, or Firm* — NSIP Law

(57) ABSTRACT

The present invention relates to a recombinant microorganism having an enhanced ability to produce heme, coproporphyrin III (Copro III), and uroporphyrin III (Uro III), and a method for producing heme, coproporphyrin III, and uroporphyrin III using same. When using a recombinant microorganism incorporating a gene that codes glutamyl-tRNA reductase (HemA), glutamate-1-semialdehyde aminotransferase (HemL), and diphtheria toxin repressor (DtxR), which is a transcription factor capable of inducing the expression of genes related to heme metabolic pathways, porphyrin-based structures can be produced at high yield, and thus the method is economic.

7 Claims, 7 Drawing Sheets
Specification includes a Sequence Listing.

(56) References Cited

OTHER PUBLICATIONS

Sasaki, Ken et al., "Production of 5-Aminolevulinic Acid by Photosynthetic Bacteria", *Journal of Fermentation Technology*, vol. 65, Issue 5, 1987, (pp. 511-515).
Tanaka, Tohru et al., "Formation of 5-aminolevulinic acid under aerobic/dark condition by a mutant of Rhodobacter Sphaeroides", Biotechnology Letters, vol. 13, Issue 8, Aug. 1991, (pp. 589-594).
Carpenter, Charles E. et al., "Contributions of Heme and Nonheme Iron to Human Nutrition", *Critical Reviews in Food Science and Nutrition*, Issue 4, 1992, (pp. 333-367).
Sasaki, Ken et al., "Effect of Culture pH on the Extracellular Production of 5-Aminolevulinic Acid by Rhodobacter Sphaeroides from Volatile Fatty Acids", *Biotechnology Letters*, vol. 15, Issue 8, Aug. 1993 (pp. 859-864).
Frankenberg, N. et al., "Bacterial heme biosynthesis and its biotechnological application", *Applied Microbiology and Biotechnology*, vol. 63, Issue 2, Dec. 2003, (pp. 115-127).
Li, Dangsheng, "PGC-1α: Looking behind the Sweet Treat for Porphyria", *Cell*, vol. 122, Issue 4, Aug. 26, 2005 (pp. 487-489).
Yang, Dong-Soo et al., "Optimizing the Production of 5-Aminolevulinic Acid by Recombinant *Escherichia coli* Containing the Rhodobacter capsulatus hemA Gene", *Korean Journal of Microbiology and Biotechnology*, vol. 37, Issue 2, Jun. 2009 (pp. 153-159).
Frunzke, Julia et al., "Control of Heme Homeostasis in Corynebacterium glutamicum by the Two-Component System HrrSA", *Journal of Bacteriology*, vol. 193, No. 5, Mar. 2011 (pp. 1212-1221).
Guo, Xiaoqing et al., "Promotive effects of 5-aminolevulinic acid on photosynthesis and chlorophyll fluorescence of tomato seedlings under suboptimal low temperature and suboptimal photon flux density stress-Short communication", *Horticultural Science*, vol. 39, Issue 2, 2012, (pp. 97-99).
Yu, Xiaoli et al., "Engineering Corynebacterium glutamicum to produce 5-aminolevulinic acid from glucose", *Microbial Cell Factories*, vol. 14, Article No. 183, 2015 (pp. 1-10).
"Multispecies: glutamate-1-semialdehyde 2,1-aminomutase [Enterobacteriaceae]", Mar. 26, 2016.
"Multispecies: diphtheria toxin repressor [Corynebacterium]", Jul. 13, 2016.
"Glutamyl-tRNA reductase [Elizabethkingia anophelis]", Aug. 31, 2016.
Korean Office Action dated Nov. 15, 2017 in counterpart Korean Patent Application No. 10-2017-0061713 (6 pages in Korean).
International Search Report dated Aug. 14, 2018 in counterpart International Patent Application No. PCT/KR2018/005740 (2 pages in English and 2 pages in Korean).

* cited by examiner

SEQUENCE LISTING

```
<160> NUMBER OF SEQ ID NOS: 14

<210> SEQ ID NO 1
<211> LENGTH: 420
<212> TYPE: PRT
<213> ORGANISM: Salmonella sp.

<400> SEQUENCE: 1

Met Thr Lys Lys Leu Leu Ala Leu Gly Ile Asn His Lys Thr Ala Pro
1               5                   10                  15

Val Ser Leu Arg Glu Arg Val Thr Phe Ser Pro Asp Thr Leu Asp Gln
            20                  25                  30

Ala Leu Asp Ser Leu Leu Ala Gln Pro Met Val Gln Gly Gly Val Val
        35                  40                  45

Leu Ser Thr Cys Asn Arg Thr Glu Leu Tyr Leu Ser Val Glu Glu Gln
    50                  55                  60

Asp Asn Leu Gln Glu Ala Leu Ile Arg Trp Leu Cys Asp Tyr His Asn
65                  70                  75                  80

Leu Asn Glu Asp Asp Leu Arg Asn Ser Leu Tyr Trp His Gln Asp Asn
                85                  90                  95
```

```
Asp Ala Val Ser His Leu Met Arg Val Ala Ser Gly Leu Asp Ser Leu
                100                 105                 110

Val Leu Gly Glu Pro Gln Ile Leu Gly Gln Val Lys Lys Ala Phe Ala
            115                 120                 125

Asp Ser Gln Lys Gly His Leu Asn Ala Ser Ala Leu Glu Arg Met Phe
        130                 135                 140

Gln Lys Ser Phe Ser Val Ala Lys Arg Val Arg Thr Glu Thr Asp Ile
145                 150                 155                 160

Gly Ala Ser Ala Val Ser Val Ala Phe Ala Cys Thr Leu Ala Arg
                165                 170                 175

Gln Ile Phe Glu Ser Leu Ser Thr Val Thr Val Leu Leu Val Gly Ala
                180                 185                 190

Gly Glu Thr Ile Glu Leu Val Ala Arg His Leu Arg Glu His Lys Val
            195                 200                 205

Gln Lys Met Ile Ile Ala Asn Arg Thr Arg Glu Arg Ala Gln Ala Leu
            210                 215                 220

Ala Asp Glu Val Gly Ala Glu Val Ile Ser Leu Ser Asp Ile Asp Ala
225                 230                 235                 240

Arg Leu Gln Asp Ala Asp Ile Ile Ile Ser Thr Ala Ser Pro Leu
                245                 250                 255

Pro Ile Ile Gly Lys Gly Met Val Glu Arg Ala Leu Lys Ser Arg Arg
            260                 265                 270

Asn Gln Pro Met Leu Leu Val Asp Ile Ala Val Pro Arg Asp Val Glu
                275                 280                 285

Pro Glu Val Gly Lys Leu Ala Asn Ala Tyr Leu Tyr Ser Val Asp Asp
            290                 295                 300

Leu Gln Ser Ile Ile Ser His Asn Leu Ala Gln Arg Gln Ala Ala
305                 310                 315                 320

Val Glu Ala Glu Thr Ile Val Glu Gln Glu Ala Ser Glu Phe Met Ala
                325                 330                 335

Trp Leu Arg Ala Gln Gly Ala Ser Glu Thr Ile Arg Glu Tyr Arg Ser
            340                 345                 350

Gln Ser Glu Gln Ile Arg Asp Glu Leu Thr Thr Lys Ala Leu Ser Ala
        355                 360                 365

Leu Gln Gln Gly Gly Asp Ala Gln Ala Ile Leu Gln Asp Leu Ala Trp
    370                 375                 380

Lys Leu Thr Asn Arg Leu Ile His Ala Pro Thr Lys Ser Leu Gln Gln
385                 390                 395                 400

Ala Ala Arg Asp Gly Asp Asp Glu Arg Leu Asn Ile Leu Arg Asp Ser
                405                 410                 415

Leu Gly Leu Glu
        420

<210> SEQ ID NO 2
<211> LENGTH: 426
<212> TYPE: PRT
<213> ORGANISM: Escherichia coli

<400> SEQUENCE: 2

Met Ser Lys Ser Glu Asn Leu Tyr Ser Ala Ala Arg Glu Leu Ile Pro
1               5                   10                  15

Gly Gly Val Asn Ser Pro Val Arg Ala Phe Thr Gly Val Gly Gly Thr
            20                  25                  30

Pro Leu Phe Ile Glu Lys Ala Asp Gly Ala Tyr Leu Tyr Asp Val Asp
        35                  40                  45
```

```
Gly Lys Ala Tyr Ile Asp Tyr Val Gly Ser Trp Pro Met Val Leu
 50                  55                  60

Gly His Asn His Pro Ala Ile Arg Asn Ala Val Ile Glu Ala Ala Glu
 65                  70                  75                  80

Arg Gly Leu Ser Phe Gly Ala Pro Thr Glu Met Glu Val Lys Met Ala
                 85                  90                  95

Gln Leu Val Thr Glu Leu Val Pro Thr Met Asp Met Val Arg Met Val
            100                 105                 110

Asn Ser Gly Thr Glu Ala Thr Met Ser Ala Ile Arg Leu Ala Arg Gly
        115                 120                 125

Phe Thr Gly Arg Asp Lys Ile Ile Lys Phe Glu Gly Cys Tyr His Gly
130                 135                 140

His Ala Asp Cys Leu Leu Val Lys Ala Gly Ser Gly Ala Leu Thr Leu
145                 150                 155                 160

Gly Gln Pro Asn Ser Pro Gly Val Pro Ala Asp Phe Ala Lys His Thr
                165                 170                 175

Leu Thr Cys Thr Tyr Asn Asp Leu Ala Ser Val Arg Ala Ala Phe Glu
            180                 185                 190

Gln Tyr Pro Gln Glu Ile Ala Cys Ile Ile Val Glu Pro Val Ala Gly
        195                 200                 205

Asn Met Asn Cys Val Pro Pro Leu Pro Glu Phe Leu Pro Gly Leu Arg
210                 215                 220

Ala Leu Cys Asp Glu Phe Gly Ala Leu Leu Ile Ile Asp Glu Val Met
225                 230                 235                 240

Thr Gly Phe Arg Val Ala Leu Ala Gly Ala Gln Asp Tyr Tyr Gly Val
                245                 250                 255

Glu Pro Asp Leu Thr Cys Leu Gly Lys Ile Ile Gly Gly Gly Met Pro
            260                 265                 270

Val Gly Ala Phe Gly Gly Arg Arg Asp Val Met Asp Ala Leu Ala Pro
        275                 280                 285

Thr Gly Pro Val Tyr Gln Ala Gly Thr Leu Ser Gly Asn Pro Ile Ala
290                 295                 300

Met Ala Ala Gly Phe Ala Cys Leu Asn Glu Val Ala Gln Pro Gly Val
305                 310                 315                 320

His Glu Thr Leu Asp Glu Leu Thr Ser Arg Leu Ala Glu Gly Leu Leu
                325                 330                 335

Glu Ala Ala Glu Glu Ala Gly Ile Pro Leu Val Val Asn His Val Gly
            340                 345                 350

Gly Met Phe Gly Ile Phe Phe Thr Asp Ala Glu Ser Val Thr Cys Tyr
        355                 360                 365

Gln Asp Val Met Ala Cys Asp Val Glu Arg Phe Lys Arg Phe His
370                 375                 380

Met Met Leu Asp Glu Gly Val Tyr Leu Ala Pro Ser Ala Phe Glu Ala
385                 390                 395                 400

Gly Phe Met Ser Val Ala His Ser Met Glu Asp Ile Asn Asn Thr Ile
                405                 410                 415

Asp Ala Ala Arg Arg Val Phe Ala Lys Leu
            420                 425

<210> SEQ ID NO 3
<211> LENGTH: 228
<212> TYPE: PRT
<213> ORGANISM: Corynebacterium glutamicum
```

<400> SEQUENCE: 3

```
Met Lys Asp Leu Val Asp Thr Thr Glu Met Tyr Leu Arg Thr Ile Tyr
1               5                   10                  15

Glu Leu Glu Glu Glu Gly Ile Val Pro Leu Arg Ala Arg Ile Ala Glu
            20                  25                  30

Arg Leu Glu Gln Ser Gly Pro Thr Val Ser Gln Thr Val Ala Arg Met
        35                  40                  45

Glu Arg Asp Gly Leu Val His Val Ser Pro Arg Ser Leu Glu Met
50                  55                  60

Thr Pro Glu Gly Arg Ser Leu Ala Ile Ala Val Met Arg Lys His Arg
65                  70                  75                  80

Leu Ala Glu Arg Leu Leu Thr Asp Ile Ile Gly Leu Asp Ile His Lys
                85                  90                  95

Val His Asp Glu Ala Cys Arg Trp Glu His Val Met Ser Asp Glu Val
            100                 105                 110

Glu Arg Arg Leu Val Glu Val Leu Asp Asp Val His Arg Ser Pro Phe
        115                 120                 125

Gly Asn Pro Ile Pro Gly Leu Gly Glu Ile Gly Leu Asp Gln Ala Asp
    130                 135                 140

Glu Pro Asp Ser Gly Val Arg Ala Ile Asp Leu Pro Leu Gly Glu Asn
145                 150                 155                 160

Leu Lys Ala Arg Ile Val Gln Leu Asn Glu Ile Leu Gln Val Asp Leu
                165                 170                 175

Glu Gln Phe Gln Ala Leu Thr Asp Ala Gly Val Glu Ile Gly Thr Glu
            180                 185                 190

Val Asp Ile Ile Asn Glu Gln Gly Arg Val Val Ile Thr His Asn Gly
        195                 200                 205

Ser Ser Val Glu Leu Ile Asp Asp Leu Ala His Ala Val Arg Val Glu
    210                 215                 220

Lys Val Glu Gly
225
```

<210> SEQ ID NO 4
<211> LENGTH: 1263
<212> TYPE: DNA
<213> ORGANISM: Salmonella sp.

<400> SEQUENCE: 4

```
atgaccaaga agcttttagc gctcggtatt aaccataaaa cggcacctgt atcgctgcga      60
gaacgcgtaa cgttttcgcc ggacacgctt gatcaggcgc tggacagcct gcttgcgcag     120
ccaatggtgc agggcggggt cgtgctgtca acctgtaacc gtacagagct gtatctgagc     180
gtggaagagc aggataacct gcaagaagcg ctgatccgct ggttatgcga ttaccataac     240
ctgaacgagg acgatctgcg caacagtctg tactggcatc aggacaatga cgccgtcagc     300
cacctgatgc gcgtcgccag cggtctggat tcactggtgc tgggcgaacc gcaaatcctc     360
ggtcaggtga aaaaagcgtt tgcggattcg caaaaaggcc accttaacgc cagcgcgctg     420
gagcgaatgt ttcagaagtc ttttccgtc gctaagcgag tcggactga aaccgatatc     480
ggcgctagcg ccgtctccgt cgcgtttgcc gcctgtacgc tcgcccgcca aatctttgaa     540
tcgctctcga cggtcaccgt actgttagtt ggcgcgggcg aaaccattga actggtggcg     600
cgtcaccctgc gcgagcataa agtacaaaag atgattatcg ccaaccgaac ccgcgagcgc     660
gcgcaagccc tggcggatga ggtaggcgct gaggttatct cgctcagcga tatcgacgcc     720
```

```
cgtttgcagg atgccgatat tattatcagt tcgaccgcca gcccgctgcc gattatcggt      780
aaaggcatgg tggagcgcgc attaaaaagc cgtcgcaacc agccgatgct gctggtggat      840
attgccgtac cgcgcgacgt tgaaccggaa gtcggcaaac tggcgaacgc ttatctttat      900
agcgtcgatg atttacagag catcatttcg cataatctgg cgcagcgtca ggctgcggca      960
gtagaagcgg aaacgattgt tgagcaggaa gccagcgagt ttatggcctg ctacgcgcc     1020 caggggggcca gcgagaccat tcgggaatac cgtagtcagt cggagcagat tcgtgacgaa     1080
ctgactacca aagcgctgtc ggcccttcaa cagggcggtg atgcgcaagc catcttgcag     1140
gatctggcat ggaaactgac caaccgcctg attcatgcgc aacgaaatc acttcaacag      1200 gctgcccgtg acggggatga cgaacgcctg aatattctgc gcgacagcct cgggctggag     1260
tag                                                                   1263

<210> SEQ ID NO 5
<211> LENGTH: 1281
<212> TYPE: DNA
<213> ORGANISM: Escherichia coli

<400> SEQUENCE: 5
atgagtaagt ctgaaaatct ttacagcgca gcgcgcgagc tgatccctgg cggtgtgaac       60
tcccctgttc gcgcctttac tggcgtgggc ggcactccac tgtttatcga aaagcggac      120 ggcgcttatc tgtacgatgt tgatggcaaa gcctatatcg attatgtcgg ttcctggggg     180
ccgatggtgc tgggccataa ccatccggca atccgcaatg ccgtgattga agccgccgag     240
cgtggtttaa gctttggtgc accaaccgaa atggaagtga aaatggcgca actggtgact      300
gaactggtcc cgaccatgga tatggtgcgc atggtgaact ccggcaccga ggcgacgatg      360
agcgccatcc gcctggcccg tggttttacc ggtcgcgaca aaattattaa atttgaaggt      420
tgttaccacg gtcacgctga ctgcctgctg gtgaaagccg ttctggcgc actcacgtta      480 ggccagccaa actcgccggg cgttccggca gatttcgcca acataccttt aacctgtact      540
tataacgatc tggcttctgt acgcgccgcg tttgagcaat acccgcaaga gattgcctgt      600
attatcgtcg agccggtggc aggcaatatg aactgcgttc caccgctgcc agagttcctg      660
ccaggtctgc gtgcgctgtg cgacgaattt ggcgcattgc tgatcatcga tgaagtaatg      720
accggcttcc gcgtggcact ggctggcgca caggattatt acggtgtgga accggatctc      780
acctgcctgg gcaaaatcat cggcggtgga atgccggtag gcgcattcgg tggtcgtcgt      840
gatgtaatgg atgcgctggc cccgacgggt ccggtctatc aggcgggtac gctttccggt      900
aacccaattg cgatggcagc gggtttcgcc tgtctgaatg aagtcgcgca gccgggcgtt      960
cacgaaacgt tggatgagct gacatcacgt ctggcagaag gtctgctgga agcggcagaa     1020
gaagccggaa ttccgctggt cgttaaccac gttggcggca tgttcggtat tttctttacc     1080
gacgccgagt ccgtgacgtg ctatcaggat gtgatggcct gtgacgtgga acgctttaag     1140
cgtttcttcc atatgatgct ggacgaaggt gtttacctgg caccgtcagc gtttgaagcg     1200
ggctttatgt ccgtggcgca cagcatggaa gatatcaata acaccatcga tgctgcacgt     1260
cgggtgtttg cgaagttgtg a                                               1281

<210> SEQ ID NO 6
<211> LENGTH: 687
<212> TYPE: DNA
<213> ORGANISM: Corynebacterium glutamicum

<400> SEQUENCE: 6
```

```
atgaaggatc tggtcgatac caccgaaatg tatctgcgca ctatttacga gctggaagaa      60
gagggcattg ttcctctgcg tgctcgtatc gcagaacgcc ttgagcagtc cggcccaact     120
gtcagccaga ctgtcgcccg tatggaacgc gacggtcttg tgcacgtcag ccccgaccgc     180
agcctcgaaa tgactccaga gggacgttcc ctcgccatcg ccgtgatgcg taagcaccgc     240
ctagcagaac gcctccttac cgacatcatc ggcttggaca tccacaaagt ccacgacgaa     300
gcatgccgct gggagcacgt gatgagtgat gaggttgaac gtcgcctcgt tgaagttctt     360
gacgatgtgc atcgctcccc tttcggtaac ccaattcctg gcctcggcga aatcggtttg     420
gatcaagcag atgagcctga ttccggcgtt cgtgccatcg atctgcctct cggtgagaac     480
ctgaaggctc gcatcgtaca gctcaacgag atcctgcagg tagatcttga gcagttccag     540
gcactcaccg acgcgggtgt tgaaatcggt accgaagtag acatcatcaa tgagcagggc     600
cgggtcgtga tcacccacaa cggctccagc gtagaactga ttgacgatct tgcacatgca     660
gtccgcgtag aaaaggttga gggctaa                                         687
```

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7

```
acgggatcca tgacccttttt agcgctcgg                                       29
```

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8

```
actgcggccg cggtacctca caacttcgca a                                     31
```

<210> SEQ ID NO 9
<211> LENGTH: 47
<212> TYPE: DNA
<213> ORGANISM: Artificial Sequence
<220> FEATURE:
<223> OTHER INFORMATION: primer

<400> SEQUENCE: 9

```
aatgcggccg caaggagata tacatgaagg atctggtcga taccacc                    47
```

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10

```
aatgcggccg cttagccctc aacctttttct acgcg                                35
```

<210> SEQ ID NO 11
<211> LENGTH: 31
<212> TYPE: DNA
<213> ORGANISM: Artificial Sequence
<220> FEATURE:

-continued

```
<223> OTHER INFORMATION: primer

<400> SEQUENCE: 11
tcgatcgata tgaccaagaa gcttttagcg c                              31

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
actggatccc tactccagcc cgaggct                                   27

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
gcaggatcca tgagtaagtc tgaaaatc                                  28

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
actggtacct cacaacttcg caa                                       23
```

RECOMBINANT MICROORGANISM HAVING ENHANCED ABILITY TO PRODUCE HEME, COPROPORPHYRIN III, AND UROPORPHYRIN III, AND METHOD FOR PRODUCING HEME, COPROPORPHYRIN III, AND UROPORPHYRIN III USING SAME

CROSS REFERENCE TO RELATED APPLICATION(S)

This application is a U.S. National Stage Application of International Application No. PCT/KR2018/005740, filed on May 18, 2018, which claims the benefit under 35 USC 119(a) and 365(b) of Korean Patent Application No. 10-2017-0061713, filed on May 18, 2017 and Korean Patent Application No. 10-2018-0056906, filed on May 18, 2018, in the Korean Intellectual Property Office, the entire disclosure of which is incorporated herein by reference for all purposes.

TECHNICAL FIELD

The present invention relates to a recombinant microorganism having enhanced capability to produce heme, coproporphyrin III (Copro III) and uroporphyrin III (Uro III), and a method of producing heme, coproporphyrin III and uroporphyrin III using the same, and more particularly, to a recombinant microorganism obtained by introducing a gene encoding a glutamyl-tRNA reductase (HemA), a gene encoding a glutamate-1-semialdehyde aminotransferase (HemL) and a gene encoding a diphtheria toxin repressor (DtxR), which is a transcription factor capable of inducing the expression of genes related to heme metabolic pathways, into a strain overproducing L-glutamic acid, which is a starting material of a metabolic pathway of porphyrin, to produce 5-aminolevulinic acid (ALA), which is a precursor of heme, coproporphyrin III and uroporphyrin III, and a method of producing heme, coproporphyrin III and uroporphyrin III using the same.

BACKGROUND ART

Heme is a porphyrin containing an iron ion (ferrous ion, $Fe^{2+}$), and is synthesized in vivo through a pathway (C4 pathway) by polymerization of succinyl-CoA and glycine, or a pathway (C5 pathway) using ATP and NADPH coenzymes from glutamate as a starting material. The preference for these two pathways varies from species to species. The heme metabolic pathway starts from the synthesis of 5-aminolevulinic acid (ALA) though the action of 5-aminolevulinic acid synthase (ALAS) for the C4 pathway, and through the action of glutamyl-tRNA synthetase (GltX), glutamyl-tRNA reductase (HemA) and glutamate-1-semialdehyde aminotransferase (HemL) from glutamate for the C5 pathway, and the synthesis of heme is completed through integration of iron ions (ferrous ions) into protoporphyrin IX (Proto IX) by ferrochelatase (HemH) (Frankenberg, N., Moser, J. & Jahn, D., Appl. Microbiol. Biotechnol. 63: 115-127, 2003).

A variety of porphyrin analogues are produced through heme biosynthesis pathway. The porphyrin analogues include porphobilinogen (PBG), 1-hydroxymethylbilane (HMB), uroporphyrin I (Uro I), uroporphyrin III (Uro III), coproporphyrin I (Copro I), coproporphyrin III (Copro III), protoporphyrin IX and the like.

Heme plays a key role in oxygen transfer, reactive oxygen removal, and electron transfer associated with energy production (Einstein, A., B. Podolsky, Cell 122: 487-489, 2005). Among porphyrin analogues and complexes, heme is of particular commercial importance. Heme can be used as a source of iron in an organic form. Organic forms of iron agents exhibit in vivo absorption rates two times higher than inorganic forms of iron agents, and are thus considered to be an excellent iron source (Crit. Rev. Food Sci. Nutr. 31: 333-367, 1992; Acta. Med. Scand. 629: 1-46, 1980). For this reason, heme is highly applicable to iron agents, anemia drugs, and iron feed or feed additives in the livestock field. In addition, in the biotechnology field, a variety of research has been conducted on application of heme, for example, improvement in protein activity and an optical sensor, and a potential as a conductive bio-plastics has been suggested through polymers synthesized from heme as a precursor. As a result, the fields of application of heme are continually expanding.

5-Aminolevulinic acid is a precursor of heme and is used as an environmentally friendly biopesticide (photoactive herbicide) and a plant growth promoter. Crops such as radishes, kidney beans, barley, potatoes, garlic, rice, corn rice and corn, which are treated with low concentrations of 5-aminolevulinic acid, have exhibited growth increased by 10 to 60% compared to groups not treated therewith (Hotta, Y., Tanaka, T., Plant Growth Regulation 22: 109-114, 1997). Also, 5-aminolevulinic acid is applicable to the pharmaceutical field. 5-aminolevulinic acid is currently used as therapeutic agents for skin diseases such as acne and atopy, skin cancer and the like, and is also used in cosmetics. In the livestock field, it can be used as a growth accelerator for replacing antibiotics in order to enhance the autoimmunity of livestock and improve feed efficiency (Korea Patent No. 10-0459918).

5-aminolevulinic acid is known to be biosynthesized by two biosynthetic systems (C4 and C5 pathways). The C4 biosynthetic system found in animals, fungi, aerobic bacteria and the like performs synthesis through condensation of glycine and succinyl-CoA. This reaction is catalyzed by a 5-aminolevulinic acid synthase, which is an enzyme dependent upon pyridoxal phosphate. Another pathway, the C5 biosynthetic system, is found in plants, algae and *Escherichia coli*. This pathway converts glutamate to 5-aminolevulinic acid by a series of reactions through glutamyl-tRNA synthetase (GltX), glutamyl-tRNA reductase (HemA) and glutamate-1-semialdehyde aminotransferase (HemL).

Currently, 5-aminolevulinic acid is produced using complex organic synthesis (Beale S I, et al., Phytochemistry, 18: 441, 1979), but is not profitable due to its high production cost. Thus, studies on the method of producing 5-aminolevulinic acid using fermentation of microorganisms such as *Rhodobacter sphaeroides, Clostridium thermoaceticum, Methanobacterium thermoautotrophicum, Agmenellum quadruplicatum, Anacystis marina* and *Chlorella vulgaris* and the use thereof have been conducted (Sasaki K., et al., J. Ferment. Technol., 65:511, 1987; Sasaki K., et al., Biotechnol. Lett., 15:859(1993); Tanaka T., et al., Biotechnol. Lett., 13:589, 1991; Janschen R., et al., FEMS Microb. Lett., 12:167, 1981; Kipe-Not J. A. and Steven S. E., Plant Physiol., 65:126, 1980; Beale S. I., and Castelfranco P. A., Plant Physiol., 53:297, 1974).

The molecular biological biosynthetic pathway of 5-aminolevulinic acid has been identified through isolation of the 5-aminolevulinic acid auxotrophic mutant strain (ALA auxotrophy). The 5-aminolevulinic acid synthase gene in the C4 pathway is found to have two isozymes, that is, hemA and hemT, while 5-aminolevulinic acid synthase gene in the C5 pathway is composed of hemA, hemL and hemM genes.

In order to increase the synthesis of 5-aminolevulinic acid through these microorganisms, there have been studies on the effects of reinforcing the precursor in the culture medium, or separating and adding lower fatty acids from organic waste resources, and on control of pH and temperature, supply of oxygen, and the increase in 5-aminolevulinic acid production by emission of light in the case of photosynthetic bacteria (Korean Journal of Microbiology and Biotechnology, Vol. 37 No. 2, pp. 153-15, 2009). However, the development of a biological method capable of efficiently producing 5-aminolevulinic acid, porphyrin, a porphyrin analogue or heme is insufficient.

Accordingly, as a result of extensive efforts to develop a recombinant microorganism having improved capability to produce heme using *Corynebacterium glutamicum*, which overproduces L-glutamic acid, which is a starting material of the C5 production pathway of heme, the present inventors have found that heme, coproporphyrin III and uroporphyrin III can be produced in high yield, compared to conventional microorganisms having capability to produce heme, when using a recombinant microorganism introduced with genes that overproduce 5-aminolevulinic acid, which is a precursor of heme, and with transcription factors that regulate the transcription of genes involved in heme synthesis in order to improve heme biosynthesis. Based on this finding, the present invention has been completed.

The above information disclosed in this Background section is provided only for better understanding of the background of the present invention and therefore it may not contain information that forms the prior art that is already known to those skilled in the field to which the present invention pertains.

DISCLOSURE

Technical Problem

Therefore, the present invention has been made in view of the above problems, and it is one object of the present invention to provide a recombinant microorganism having improved capability to produce heme, coproporphyrin III (Copro III) and uroporphyrin III (Uro III).

It is another object of the present invention to provide a method of producing heme by culturing the recombinant microorganism in a medium containing an iron ion (ferrous ion, $Fe^{2+}$).

It is another object of the present invention to provide a method of producing coproporphyrin III (Copro III) by culturing the recombinant microorganism.

It is another object of the present invention to provide a method of producing uroporphyrin III (Uro III) by culturing the recombinant microorganism.

Technical Solution

In accordance with one aspect of the present invention, the above and other objects can be accomplished by the provision of a recombinant microorganism produced by introducing a gene encoding a glutamyl-tRNA reductase (HemA), a gene encoding a glutamate-1-semialdehyde aminotransferase (HemL) and a gene encoding a diphtheria toxin repressor (DtxR) into a microorganism having the capability to produce glutamic acid.

In accordance with another aspect of the present invention, there is provided a method of producing heme including (a) culturing the recombinant microorganism in a medium containing an iron ion (ferrous ion, $Fe^{2+}$) to produce heme and (b) extracting and collecting the produced heme.

In accordance with another aspect of the present invention, there is provided a method of producing coproporphyrin III (Copro III) including (a) culturing the recombinant microorganism to produce coproporphyrin III (Copro III) and (b) collecting the produced coproporphyrin III (Copro III).

In accordance with another aspect of the present invention, there is provided a method of producing uroporphyrin III (Uro III) including (a) culturing the recombinant microorganism to produce uroporphyrin III (Uro III) and (b) collecting the produced uroporphyrin III (Uro III).

BEST MODE

Unless defined otherwise, all technical and scientific terms used herein have the same meanings as those appreciated by those skilled in the art to which the present invention pertains. In general, the nomenclature used herein is well-known in the art and is ordinarily used.

Figure 8:
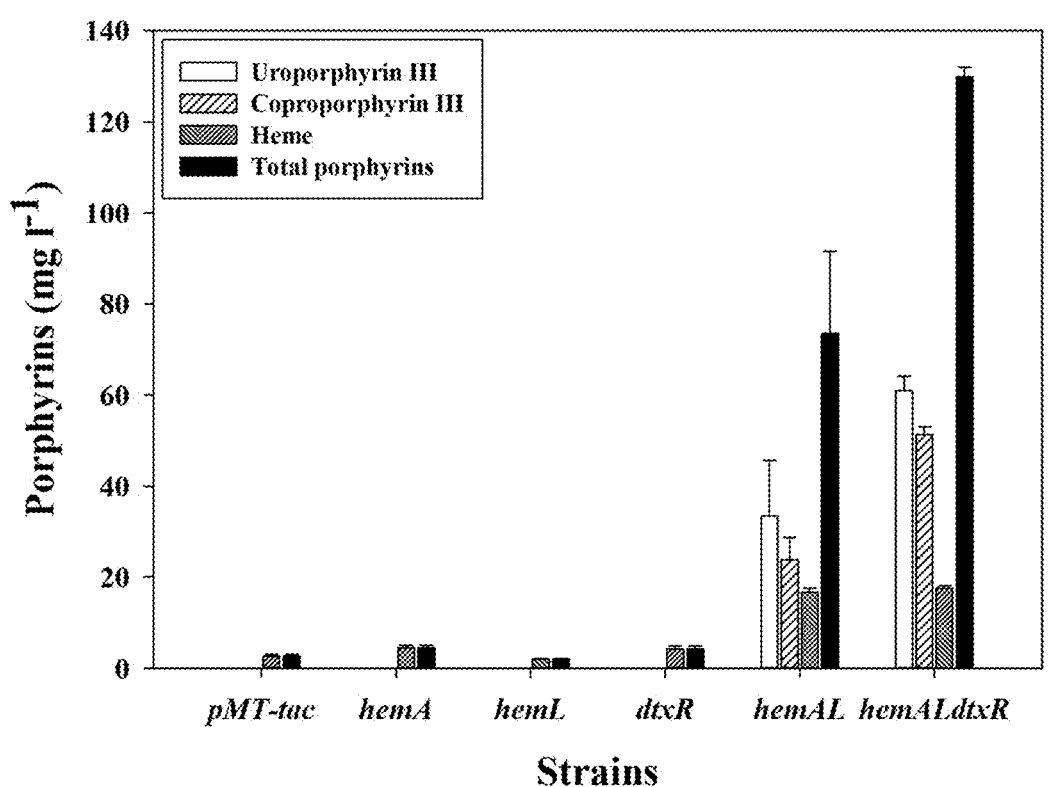
FIG. 8 shows the results of production yields of heme, coproporphyrin III (Copro III), uroporphyrin III (Uro III) and total porphyrin by a wild-type strain and respective recombinant microorganisms.

The present invention identified that a recombinant microorganism, which is produced by introducing a gene encoding a glutamyl-tRNA reductase (HemA), a gene encoding a glutamate-1-semialdehyde aminotransferase (HemL) and a gene encoding a diphtheria toxin repressor (DtxR), which is a transcription factor that can induce the expression of genes associated with a heme metabolic pathway, to produce 5-aminolevulinic acid (ALA), which is a precursor of heme, coproporphyrin III and uroporphyrin III, using a strain that overproduces L-glutamic acid, which is a starting material of a metabolic pathway of porphyrin, can produce heme, coproporphyrin III and uroporphyrin III in high yield (FIG. 8).

Thus, in one aspect, the present invention is directed to a recombinant microorganism produced by introducing a gene encoding a glutamyl-tRNA reductase, a gene encoding a glutamate-1-semialdehyde aminotransferase and a gene encoding a diphtheria toxin repressor into a microorganism having the capability to produce glutamic acid.

The present invention is characterized in that the recombinant microorganism has improved capability (capacity) to produce heme, coproporphyrin III and uroporphyrin III.

The present invention is characterized in that the glutamyl-tRNA reductase is set forth in the amino acid sequence of SEQ ID NO: 1.

The present invention is characterized in that the glutamate-1-semialdehyde aminotransferase is set forth in the amino acid sequence of SEQ ID NO: 2.

The present invention is characterized in that the diphtheria toxin repressor is set forth in the amino acid sequence of SEQ ID NO: 3.

In the present invention, the glutamyl-tRNA reductase (HemA), the glutamate-1-semialdehyde aminotransferase (HemL) and the diphtheria toxin repressor (DtxR) are hereinafter referred to as HemA, HemL and DtxR, respectively.

In the present invention, the microorganism having the capability to produce glutamic acid may be *Corynebacterium glutamicum*.

As used herein, the term "vector" means a DNA product containing a DNA sequence operably linked to a control sequence capable of expressing DNA in a suitable host. The vector may be a plasmid, a phage particle or a simple potential genome insert. Once the vector is transformed with an appropriate host, it may replicate and function independently of the genome of the host, or may often be integrated into the genome itself. Since the plasmid is the most commonly used type of vector, the terms "plasmid" and "vector" may be used interchangeably throughout the specification of the present invention.

For the purpose of the present invention, a plasmid vector is preferably used. A typical plasmid vector that can be used for this purpose includes (a) a replication origin to efficiently conduct replication so as to include several to several hundred plasmid vectors per host cell, (b) an antibiotic resistance gene to select a host cell transformed with the plasmid vector, and (C) a restriction enzyme cleavage site into which a foreign DNA fragment is inserted. Even if an appropriate restriction enzyme cleavage site is not present, the vector and foreign DNA can be easily ligated using a synthetic oligonucleotide adapter or a linker according to a conventional method.

As used herein, the term "recombinant vector" commonly refers to a recombinant carrier, into which a fragment of heterologous DNA is inserted, and generally means a fragment of double-stranded DNA. Herein, the heterologous DNA means exogenous DNA that is not naturally found in the host cell. Once an expression vector is present in a host cell, it can replicate independently of the host chromosomal DNA, and several copies of the vector and inserted (heterologous) DNA thereof can be produced.

After ligation, the gene or the recombinant vector is transformed or transfected into a host cell. "Transformation" or "Transfection" may be carried out using various techniques commonly used to introduce foreign nucleic acids (DNA or RNA) into prokaryotic or eukaryotic host cells, for example, electrophoresis, calcium phosphate precipitation, DEAE-dextran transfection or lipofection.

The vector used to overexpress genes according to the present invention may be selected from among expression vectors well-known in the art.

As is well known in the art, in order to increase the expression level of a transgene in a host cell, the corresponding gene should be operably linked to a transcriptional/translational expression control sequence that functions in a selected expression host. Preferably, the expression control sequence and the corresponding gene are included in one recombinant vector containing both a bacterial selection marker and a replication origin. When the expression host is a eukaryotic cell, the recombinant vector should further include a useful expression marker in the eukaryotic expression host.

The host cell transformed with the recombinant vector described above constitutes another aspect of the present invention. As used herein, the term "transformation" means introduction of DNA into a host and allowing the DNA to be replicated by an extrachromosomal factor or chromosomal integration. It should be understood that not all vectors function identically in expressing the DNA sequences of the present invention. Likewise, not all hosts function identically for the same expression system. However, those skilled in the art will be able to make appropriate selections from among a variety of vectors, expression control sequences and hosts without excessive burden of experimentation and without departing from the scope of the present invention. For example, selection of a vector should be carried out in consideration of a host because the vector should be replicated therein. The number of replications of the vector, the ability to control the number of replications, and the expression of other proteins encoded by the corresponding vector, such as the expression of antibiotic markers, should also be considered.

In the present invention, preferred host cells are prokaryotic cells. Suitable prokaryotic host cells include, but are not limited to, *C. glutamicum* ATCC 13826, *C. glutamicum* ATCC 13032, *C. glutamicum* ATCC 13761, *C. glutamicum* ATCC 13058, *C. glutamicum* ATCC 14067, *C. glutamicum* ATCC 13058, *C. glutamicum* ATCC 13745 and the like. Also, *E. coli* strains such as *E. coli* DH5α, *E. coli* JM101, *E. coli* TOP10, *E. coli* K12, *E. coli* W3110, *E. coli* X1776, *E. coli* XL1-Blue (Stratagene), *E. coli* B and *E. coli* BL21 and various species and genera of other prokaryotes can be used.

Figure 9:
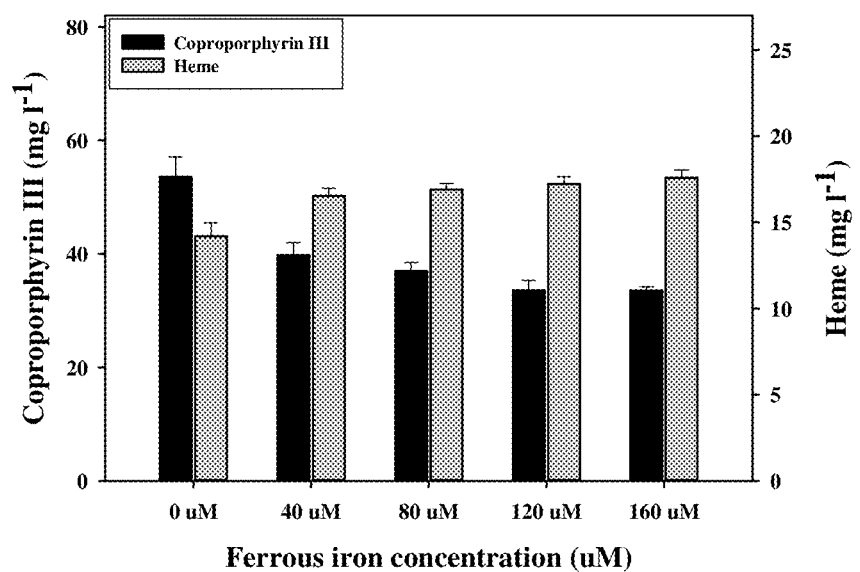
FIG. 9 shows the result of heme production yield by the recombinant microorganism depending on the iron ion ($Fe^{2+}$) concentration.

In the present invention, after culturing the recombinant microorganism into which the genes encoding HemA, HemL and DtxR are introduced in a medium containing an iron ion (ferrous ion, $Fe^{2+}$), heme is extracted through acetone-acid treatment and production yields are compared. As shown in FIG. 9, the result showed that heme production yield was the highest at the iron ion (ferrous ion) concentration of 160 μM.

In another aspect, the present invention is directed to a method of producing heme including (a) culturing the recombinant microorganism in a medium containing an iron ion (ferrous ion, $Fe^{2}$) to produce heme and (b) extracting and collecting the produced heme.

In the present invention, the iron ion is added to activate the dtxR gene. Preferably 10 to 200 µM of an iron ion (Fe$_2$SO$_4$) is added, more preferably 160 µM of an iron ion is added.

The present invention is characterized in that the extraction of heme is carried out using an acetone-acid treatment method.

The present invention is characterized in that the acid used for the acetone-acid treatment method is hydrogen chloride (HCl).

The present invention is characterized in that the acetone-acid treatment method is carried out using a mixture consisting of 99% acetone and 1.6M hydrogen chloride (HCl) at a ratio of 95:5.

In the present invention, it is identified that the recombinant microorganism introduced with genes encoding HemA, HemL and DtxR has a higher production yield of coproporphyrin III and uroporphyrin III than that of the *Corynebacterium glutamicum* wild-type strain (FIG. 8).

Thus, in another aspect, the present invention is directed to a method of producing coproporphyrin III (Copro III) including (a) culturing the recombinant microorganism to produce coproporphyrin III (Copro III) and (b) collecting the produced coproporphyrin III (Copro III).

In another aspect, the present invention is directed to a method of producing uroporphyrin III (Uro III) including (a) culturing the recombinant microorganism to produce uroporphyrin III (Uro III) and (b) collecting the produced uroporphyrin III (Uro III).

Hereinafter, the present invention will be described in more detail with reference to examples. However, it will be obvious to those skilled in the art that these examples are provided only for illustration of the present invention and should not be construed as limiting the scope of the present invention based on the subject matter of the present invention.

Example 1: Acquisition of hemA, hemL and dtxR Genes

The hemA and hemL genes were obtained from conventional expression recombinant vectors for producing 5-aminolevulinic acid (Korean Patent No. 10-1326255), and the dtxR gene was obtained from *Corynebacterium glutamicum* genomic DNA. For cloning each gene with a pMT-tac vector, the expression of which is regulated by lacI and has a high expression tac promoter, each of forward and reverse primers including the corresponding restriction enzyme sequence of the vector is synthesized, and PCR is performed using the synthesized primers.

As a result, a 1263 bp hemA gene, 1263 bp hemL gene and a 2562 bp hemAL gene were obtained, and a 687 bp dtxR gene was obtained. The amino acid sequence of the HemA is set forth in SEQ ID NO: 1, the amino acid sequence of the hemL is set forth in SEQ ID NO: 2, the amino acid sequence of DtxR is set forth in SEQ ID NO: 3, the nucleotide sequence of the hemA gene is set forth in SEQ ID NO: 4, the nucleotide sequence of the hemL gene is set forth in SEQ ID NO: 5, and the nucleotide sequence of the dtxR gene is set forth in SEQ ID NO: 6.

TABLE 1

| | Primer base sequence |
|---|---|
| SEQ ID NO 7 | ACG GGATCC ATGACCCTTTTAGCGCTCGG |
| SEQ ID NO 8 | ACT GCGGCCGC GGTACCTCACAACTTCGCAA |
| SEQ ID NO 9 | AAT GCGGCCGC AAGGAGATATACATGAAGGATCTGGTCGATACCACC |
| SEQ ID NO 10 | AAT GCGGCCGC TTAGCCCTCAACCTTTTCTACGCG |
| SEQ ID NO 11 | TCG ATCGAT ATGACCAAGAAGCTTTTAGCGC |
| SEQ ID NO 12 | ACT GGATCC CTACTCCAGCCCGAGGCT |
| SEQ ID NO 13 | GCA GGATCC ATGAGTAAGTCTGAAAATC |
| SEQ ID NO 14 | ACT GGTACC TCACAACTTCGCAA |

Example 2: Introduction of Acquired hemA and hemL Genes into pMT-Tac Vector and Transformation of Constructed Recombinant Vectors into *E. coli* and *Corynebacterium glutamicum* Strains In order to construct a recombinant vector expressing HemA, a PCR fragment containing the hemA gene obtained in Example 1 and a pMT-tac vector having a high expression tac promoter, the expression of which is regulated by lacI (Korean Patent Registration No. 10-1756338) were treated with the restriction enzymes, BamH1 and Cla1, and a ligation reaction was performed. Then, the recombinant vector was transformed into an *E. coli* DH5a strain (wild-type *Escherichia coli*) and a *Corynebacterium glutamicum* KCTC 3017 strain.

Figure 1:
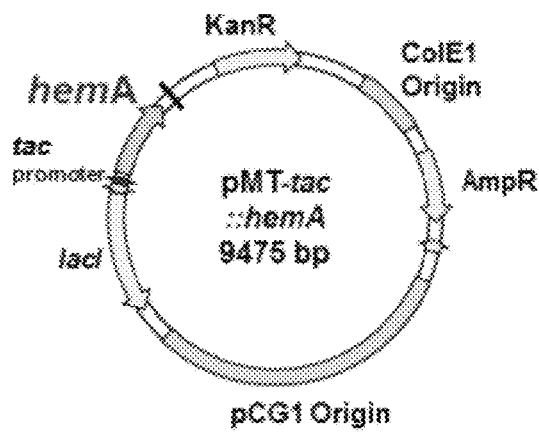
FIG. 1 shows the structure of the recombinant vector (pMT-tac:::hemA) for overexpression of glutamyl-tRNA reductase (HemA) in *E. coli* and *Corynebacterium glutamicum*.

The transformed recombinant vector is as shown in FIG. 1, and is referred to as "pMT-tac::hemA". The recombinant microorganism obtained by inserting the recombinant vector of FIG. 1 into *Escherichia coli* is referred to as "*E. coli* DH5a pMT-tac::hemA", and the recombinant microorganism obtained by inserting the recombinant vector of FIG. 1 into *Corynebacterium glutamicum* KCTC 3017 is referred to as "*Corynebacterium glutamicum* KCTC 3017 pMT-tac::hemA".

In order to construct a recombinant vector expressing HemL, a PCR fragment containing the hemL gene obtained in Example 1 and a pMT-tac vector having a high expression tac promoter, the expression of which is regulated by lacI (Korean Patent Registration No. 10-1756338), were treated with the restriction enzymes BamH1 and Kpn1, and a ligation reaction was performed. Then, the recombinant vector was transformed into an *E. coli* DH5a strain (wild-type *Escherichia coli*) and a *Corynebacterium glutamicum* KCTC 3017 strain.

Figure 2:
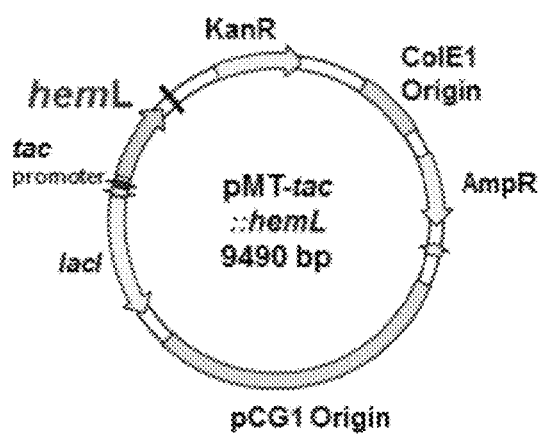
FIG. 2 shows the structure of the recombinant vector (pMT-tac:::hemL) for overexpression of glutamate-1-semialdehyde aminotransferase (HemL) in *E. coli* and *Corynebacterium glutamicum*.

The transformed recombinant vector is as shown in FIG. 2, and is referred to as "pMT-tac::hemL". The recombinant microorganism obtained by inserting the recombinant vector of FIG. 2 into *Escherichia coli* is referred to as "*E. coli* DH5a pMT-tac::hemL" and the recombinant microorganism obtained by inserting the recombinant vector of FIG. 2 into *Corynebacterium glutamicum* KCTC 3017 is referred to as "*Corynebacterium glutamicum* KCTC 3017 pMT-tac::hemL".

In order to construct a recombinant vector expressing both HemA and HemL, a PCR fragment containing the HemA and hemL genes obtained in Example 1 and a pMT-tac vector having a high expression tac promoter, the expression of which is regulated by lacI were treated with restriction enzymes, BamH1 and Not1, and a ligation reaction was performed. Then, the recombinant vector was transformed into an *E. coli* DH5a strain (wild-type *Escherichia coli*) and a *Corynebacterium glutamicum* KCTC 3017 strain.

Figure 3:
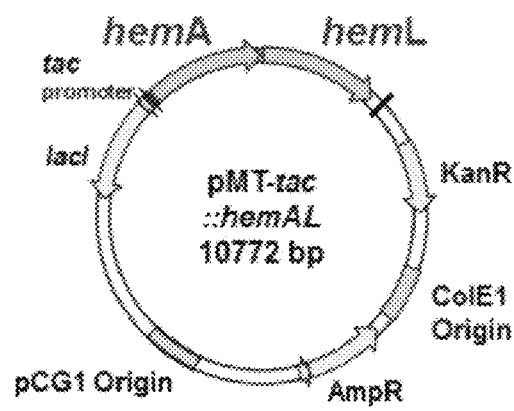
FIG. 3 shows the structure of the recombinant vector (pMT-tac:::hemAL) for overexpression of glutamyl-tRNA reductase (HemA) and glutamate-1-semialdehyde aminotransferase (HemL) in *E. coli* and *Corynebacterium glutamicum*.

The transformed recombinant vector is as shown in FIG. 3, and is referred to as "pMT-tac::hemAL". The recombinant microorganism obtained by inserting the recombinant vector of FIG. 3 into *Escherichia coli* is referred to as "*E. coli* DH5a pMT-tac::hemAL" and the recombinant microorganism obtained by inserting the recombinant vector of FIG. 3 into *Corynebacterium glutamicum* KCTC 3017 is referred to as "*Corynebacterium glutamicum* KCTC 3017 pMT-tac::hemAL".

Example 3: Introduction of Acquired dtxR Gene Into pMT-Tac Vector and Transformation of Constructed Recombinant Vector into *E. coli* and *Corynebacterium Glutamicum* Strains In order to construct a recombinant vector expressing DtxR, a PCR fragment containing the dtxR gene obtained in Example 1 and a pMT-tac vector having a high expression tac promoter, the expression of which is regulated by lacI, were treated with a restriction enzyme, Not1, and a ligation reaction was performed. Then, the recombinant vector was transformed into an *E. coli* DH5a strain (wild-type *Escherichia coli*) and a *Corynebacterium glutamicum* KCTC 3017 strain.

Figure 4:
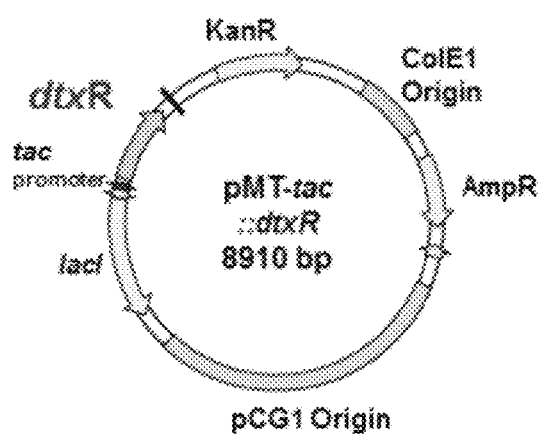
FIG. 4 shows the structure of the recombinant vector (pMT-tac:::dtxR) for overexpression of diphtheria toxin repressor (DtxR) in *E. coli* and *Corynebacterium glutamicum*.

The transformed recombinant vector is as shown in FIG. 4, which is referred to as "pMT-tac::dtxR". The recombinant microorganism obtained by inserting the recombinant vector of FIG. 4 into *Escherichia coli* is referred to as "*E. coli* DH5a pMT-tac::dtxR" and the recombinant microorganism obtained by inserting the recombinant vector of FIG. 4 into *Corynebacterium glutamicum* KCTC 3017 is referred to as "*Corynebacterium glutamicum* KCTC 3017 pMT-tac::dtxR".

Example 4: Introduction of Acquired hemA, hemL And dtxR Genes into pMT-Tac Vector and Transformation of Constructed Recombinant Vector into *E. coli* and *Corynebacterium glutamicum* Strains In order to construct a recombinant vector expressing HemA, HemL and DtxR, a PCR fragment containing the dtxR gene obtained in Example 1 and a pMT-tac::hemAL vector produced in Example 2 were treated with a restriction enzyme, Not1, and a ligation reaction was performed. Then, the recombinant vector was transformed into an *E. coli* DH5a strain and a *Corynebacterium glutamicum* KCTC 3017 strain.

Figure 5:
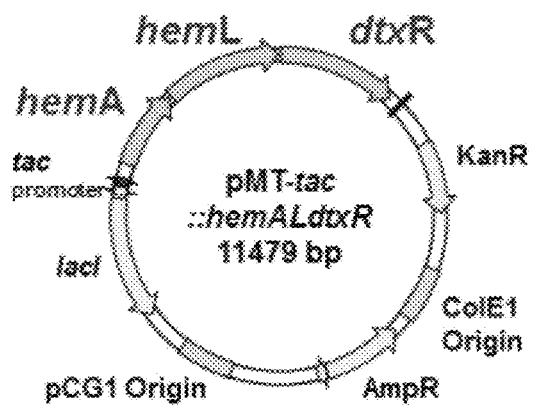
FIG. 5 shows the structure of the recombinant vector (pMT-tac:::hemALdtxR) for overexpression of glutamyl-tRNA reductase (HemA), glutamate-1-semialdehyde aminotransferase (HemL) and diphtheria toxin repressor (DtxR) in *E. coli* and *Corynebacterium glutamicum*.
Figure 6:
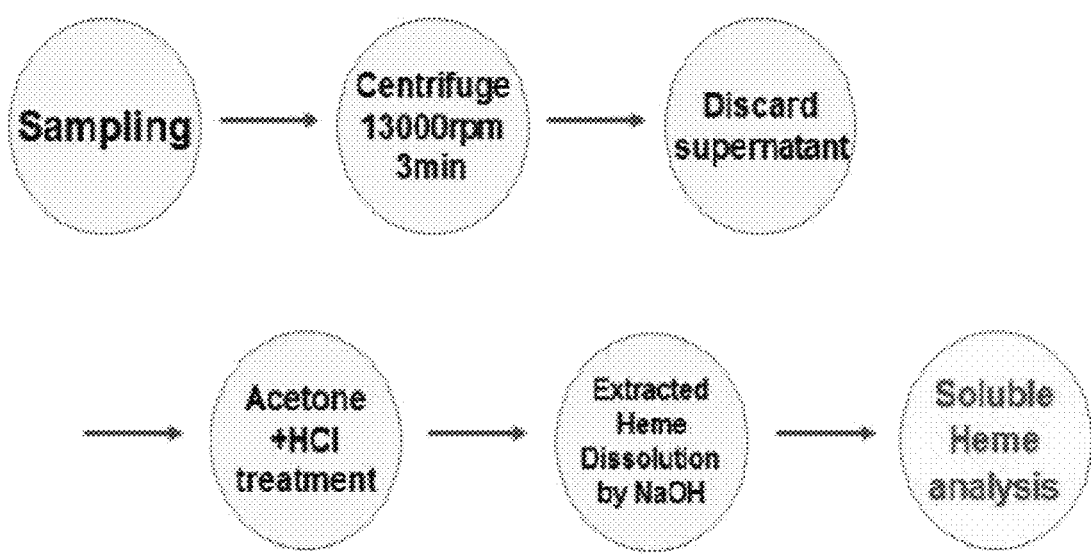
FIG. 6 is a schematic diagram illustrating a method of obtaining heme from recombinant *Corynebacterium glutamicum*.

The transformed recombinant vector is as shown in FIG. 5, and is referred to as "pMT-tac::hemALdtxR". The recombinant microorganism obtained by inserting the recombinant vector of FIG. 5 into *Escherichia coli* is referred to as "*E. coli* DH5a pMT-tac::hemALdtxR" and the recombinant microorganism obtained by inserting the recombinant vector of FIG. 5 into *Corynebacterium glutamicum* KCTC 3017 is referred to as "*Corynebacterium glutamicum* KCTC 3017 pMT-tac::hemALdtxR".

Figure 7:
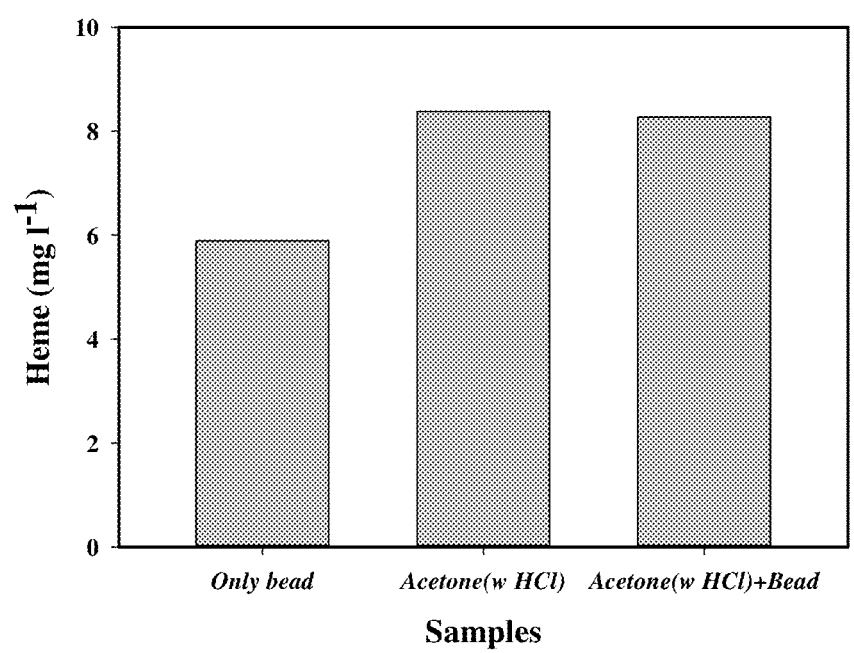
FIG. 7 shows a heme production yield depending on the extraction method of heme produced from recombinant microorganisms.

Example 5: Acetone (Addition of Hydrogen Chloride) Extraction Method of Heme Produced from Recombinant Microorganisms and Experiment for Comparing Heme Production Amount Between Wild-Type Strain and Each Recombination Microorganism Using Method An acetone (hydrogen chloride (HCl) addition) heme extraction method was conducted using the resultant product obtained by culturing *Corynebacterium glutamicum* KCTC 3017 pMT-tac::hemALdtxR prepared in Example 4. The recombinant microorganism was cultured in a flask having 50 mL CGXII liquid medium (The medium contains 20 g $(NH_4)_2SO_4$, 5 g urea, 1 g $K_2HPO_4$, 1 g $KH_2PO_4$, 10 mg $CaCl_2$, 0.25 g $MgSO_4.7H_2O$, 10 mg $FeSO_4.7H_2O$, 10 mg $MnSO_4.H_2O$, 1 mg $ZnSO_4.7H_2O$, 0.31 mg $CuSO_4.5H_2O$, 0.02 mg $NiCl_2.6H_2O$, and 0.2 mg biotin in 1 L of distilled water) containing 4% glucose at 30° C. and 150 rpm for 72 hours under conditions allowing HemA, HemL and DtxR proteins to be expressed with IPTG (isopropyl (β-D-1-thiogalactopyranoside). After 72 hours of culture, the resulting culture was centrifuged at 13,000 rpm and at 4° C. for 5 minutes, and the residual culture solution was removed in order to obtain cells in the form of pellets. The cell pellets were treated with a mixture of 99% acetone and 1.6 M hydrogen chloride (HCl) (95:5), disrupted by vortexing for 30 seconds, and diluted in 0.1N sodium hydroxide (NaOH). The overall schematic diagram of this extraction method is as shown in FIG. 4. The concentration of heme thus produced was measured through high-performance liquid chromatography (HPLC), and, as shown in FIG. 7, the results of the analysis showed that the acetone-acid treatment method using the optimized mixture (95:5) of 99% acetone and 1.6 M hydrogen chloride (HCl) increased heme extraction by 1.42 times compared to the physical cell disruption method using beads.

Production yields of heme in each of the recombinant microorganisms prepared in Examples 2, 3 and 4 and the *Corynebacterium glutamicum* wild-type strain were measured by comparing the hemes extracted using the acetone-acid treatment method. The *Corynebacterium glutamicum* recombinant microorganisms and wild-type strain were cultured in a flask having 100 mL CGXII liquid medium containing 4% glucose supplemented with 160 μM of an iron ion ($Fe^{2+}$) at 30° C. and 150 rpm for 72 hours under conditions allowing each protein to be expressed with IPTG, and other aspects of the analysis method are the same as set forth above. As can be seen from FIG. 8, the recombinant microorganisms introduced with hemA, hemL and dtxR genes showed the highest heme production yield and 6.7 times higher heme production yield compared to the *Corynebacterium glutamicum* wild-type strain.

Example 6: Comparison in Heme Production Yield of Recombinant Microorganism Expressing HemA, HemL and DtxR Depending on Iron (Ferrous) Ion Concentration In order to optimize culture conditions for activating the dtxR gene using *Corynebacterium glutamicum* KCTC 3017 pMT-tac::hemALdtxR prepared in Example 4, the production yield of heme according to the concentration of the iron ion (ferrous ion, $Fe^{2+}$) in the culture medium was compared. Culture was carried out in a flask having 100 mL CGXII liquid medium under the conditions allowing each protein to be expressed with IPTG, at 30° C. and 150 rpm for 72 hours, and 40, 80, 120 and 160 μM of iron ions ($Fe_2SO_4$) were added to each flask, and the analysis methods were performed in the same manner as in Example 5. As can be seen from FIG. 9, the production yield of heme was the highest at an iron ion concentration ($Fe^{2+}$) of 160 μM.

Example 7: Comparison in Coproporphyrin III and Uroporphyrin III Production Between Wild-Type Strain and Each Recombinant Microorganism Production of Coproporphyrin III and Uroporphyrin III in each of the recombinant microorganisms prepared in Examples 2, 3 and 4 and *Corynebacterium glutamicum* wild-type strain was carried out by obtaining the supernatant of the strain culture. The *Corynebacterium glutamicum* recombinant microorganisms and wild-type strain were cultured in a flask having 100 mL CGXII liquid medium containing 4% glucose at 30° C. and 150 rpm for 72 hours under conditions allowing each protein to be expressed with IPTG. The concentrations of Coproporphyrin III and Uroporphyrin III thus produced were measured at a wavelength of 400 nm by HPLC. As shown in FIG. 8, compared to the recombinant microorganism introduced with hemA and hemL genes, the recombinant microorganism further overexpressing dtxR showed the highest production yields of Coproporphyrin III and Uroporphyrin III among all the recombinant microorganisms and *Corynebacterium glutamicum* wild-type strain.

Figure 10:
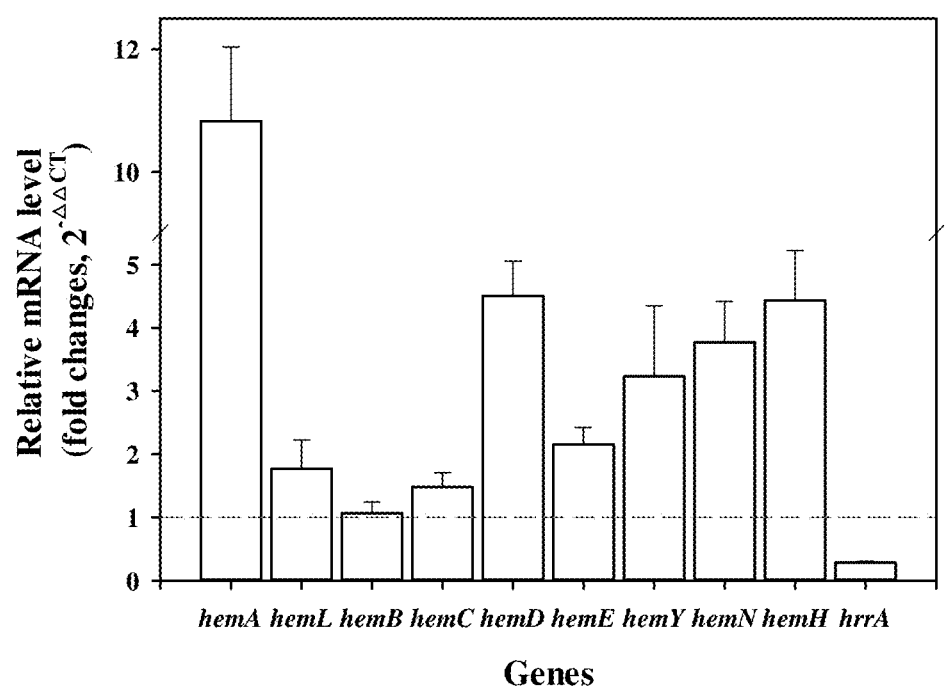
FIG. 10 shows the result of comparison of the relative messenger RNA expression levels between recombinant microorganisms expressing HemA and HemL, and recombinant microorganisms expressing HemA, HemL and DtxR.

Example 8: Experiment for Comparing Relative Messenger RNA (mRNA) Expression Levels Between Recombinant Microorganism Expressing HemA and HemL, and Recombinant Microorganism Expressing HemA, HemL and DtxR Relative messenger RNA (mRNA) expression level was compared between *Corynebacterium glutamicum* KCTC 3017 pMT-tac::hemALdtxR prepared in Example 4 and *Corynebacterium glutamicum* KCTC 3017 pMT-tac::hemAL prepared in Example 2. The *Corynebacterium glutamicum* recombinant microorganisms and wild-type strains were cultured at 30° C. and 150 rpm for 12 hours in a flask having 100-ml CGXII liquid medium containing 4% glucose under conditions allowing each protein to be expressed with IPTG. Total RNA was extracted from the sample obtained through the culturing and synthesized into cDNA through reverse transcriptase (Bioneer, M-MLV reverse transcriptase), and the levels of messenger RNA were compared through real-time PCR analysis (Qiagen) based on SYBR green. The expression level of the messenger RNA of *Corynebacterium glutamicum* KCTC 3017 pMT-tac::hemAL prepared in Example 2 was set to 1 and was compared with *Corynebacterium glutamicum* KCTC 3017 pMT-tac::hemALdtxR prepared in Example 4. As shown in FIG. 10, the recombinant *Corynebacterium glutamicum* prepared in Example 4 expressing DtxR along with HemA and HemL had higher relative messenger RNA expression levels of genes related to heme and porphyrin biosynthetic pathways (hemA, hemL, hemB, hemC, hemD, hemE and hemY) than the recombinant *Corynebacterium glutamicum* prepared in Example 2. However, the relative messenger RNA expression level of the hrrA gene, encoding the transcriptional regulator HrrA, which inhibits the expression of heme metabolic pathway genes, was further decreased. This means that the additional expression of DtxR enhances messenger RNA expression of heme metabolic pathways.

Although specific configurations of the present invention have been described in detail, those skilled in the art will appreciate that this description is provided as preferred embodiments for illustrative purposes and should not be construed as limiting the scope of the present invention. Therefore, the substantial scope of the present invention is defined by the accompanying claims and equivalents thereto.

INDUSTRIAL APPLICABILITY

Porphyrin-based structures can be produced at high yield using a recombinant microorganism introduced with a gene encoding a glutamyl-tRNA reductase (HemA), a gene encoding a glutamate-1-semialdehyde aminotransferase (HemL) and a gene encoding a diphtheria toxin repressor (DtxR) according to the present invention, and heme, coproporphyrin III (Copro III) and uroporphyrin III (Uro III) can be produced at high economic efficiency by controlling the expression of genes associated with heme metabolic pathways in which a variety of enzymes with involved with only one transcription factor, diphtheria toxin repressor (DtxR).

SEQUENCE LISTING FREE TEXT

An electronic file is attached.

The invention claimed is:

1. A recombinant microorganism produced by transforming a host microorganism with at least one vector comprising a gene encoding a glutamyl-tRNA reductase (HemA), a gene encoding a glutamate-1-semialdehyde aminotransferase (HemL), and a gene encoding a diphtheria toxin repressor (DtxR),
   wherein the glutamyl-tRNA reductase (HemA) comprises the amino acid sequence of SEQ ID NO: 1,
   wherein the glutamate-1-semialdehyde aminotransferase (HemL) comprises the amino acid sequence of SEQ ID NO: 2,
   wherein the diphtheria toxin repressor (DtxR) comprises the amino acid sequence of SEQ ID NO: 3,
   wherein the host microorganism is *Corynebacterium glutamicum*,
   wherein the recombinant microorganism overexpresses the HemA, the HemL, and the DtxR as compared to a corresponding wild-type microorganism, and
   wherein the recombinant microorganism has improved capability to produce heme, coproporphyrin III, and uroporphyrin III as compared to a corresponding wild-type microorganism.

2. A method of producing heme comprising:
   (a) culturing the recombinant microorganism according to claim 1 in a medium containing an iron ion (ferrous ion, $Fe^{2+}$) to produce heme; and
   (b) extracting and collecting the produced heme.

3. The method according to claim 2, wherein the extraction of (b) is carried out using an acetone-acid treatment method.

4. The method according to claim 3, wherein the acid is hydrogen chloride (HCl).

5. The method according to claim 2, wherein a concentration of the iron ion (ferrous ion, $Fe^{2+}$) present in the medium in (a) is 10 to 200 μM.

6. A method of producing coproporphyrin III (Copro III) comprising:
   (a) culturing the recombinant microorganism according to claim 1 to produce coproporphyrin III (Copro III); and
   (b) collecting the produced coproporphyrin III (Copro III).

7. A method of producing uroporphyrin III (Uro III) comprising:
   (a) culturing the recombinant microorganism according to claim 1 to produce uroporphyrin III (Uro III); and
   (b) collecting the produced uroporphyrin III (Uro III).

* * * * *